United States Patent [19]
Lee et al.

[11] Patent Number: 6,133,424
[45] Date of Patent: Oct. 17, 2000

[54] PPRB[110]- NUCLEAR PHOSPHOPROTEIN-THE RETINOBLASTOMA SUSCEPTIBILITY GENE PRODUCT

[75] Inventors: Wen-Hwa Lee; Eva Y. -H. P. Lee, both of San Diego, Calif.

[73] Assignee: The Regents of the University of California, Oakland, Calif.

[21] Appl. No.: 08/485,042

[22] Filed: Jun. 7, 1995

Related U.S. Application Data

[63] Continuation of application No. 08/225,099, Apr. 8, 1994, Pat. No. 5,578,701, which is a continuation of application No. 08/079,207, Jun. 17, 1993, abandoned, which is a continuation of application No. 07/914,039, Jul. 14, 1992, abandoned, which is a continuation of application No. 07/550,877, Jul. 11, 1990, abandoned, which is a division of application No. 07/098,612, Sep. 17, 1987, Pat. No. 4,942,123.

[51] Int. Cl.$^7$ ............................ C07K 14/47; A61K 38/17
[52] U.S. Cl. ........................ 530/358; 530/350; 530/352; 530/395
[58] Field of Search .............................. 424/185.1, 277.1; 530/350, 352, 358, 395; 536/23.4, 23.5

[56] References Cited

PUBLICATIONS

Angier, N., *Discover* Mar.:85–96 (1987).
Benedict et al., *Cancer Genet. and Cytogenet.* 10:311–333 (1983).
Benedict et al., *Science* 219:973–975 (1983).
Cavenee et al., *Am. J. Hum. Genet.* 36:10–24 (1984).
Cavenee et al., *Nature* 305:779–784 (1983).
Dryja et al., *Proc. Natl. Acad. Sci. USA* 83:7391–7394 (1986).
Friend et al., *Nature* 323:643–646 (1986).
Fung et al., *Science* 236:1657–1661 (1987).
Harris, Henry, *Nature* 323:582–583 (1986).
Lee et al., *Proc. Natl. Acad. Sci. USA* 83:6337–6341 (1986).
Lee et al., *Proc. Natl. Acad. Sci. USA* 83:6790–6794 (1986).
Lee et al., *Science* 235:1394–1399 (1987).
Murphree et al., *Science* 223:1028–1033 (1984).
Strong et al., *Science* 213:1501–1503 (1981).
Lee et al., *Nature* 329:642–645, Oct. 15, 1987.
Friend et al., *Proc. Natl. Acad. Sci. USA* 84:9059–9063, Dec. 1987.

*Primary Examiner*—Robert D. Budens
*Attorney, Agent, or Firm*—Townsend and Townsend and Crew

[57] ABSTRACT

This invention relates in general to a phosphoprotein product of the retinoblastoma susceptibility gene. In particular, this invention relates to a phosphoprotein ppRB$^{110}$ primarily located in the cell nucleus which has a DNA binding activity. The invention also relates to the amino acid sequence of the phosphoprotein and to the specific purified anti-retinoblastoma phosphoprotein antibody. The invention further relates to a method of diagnosing retinoblastoma and other retinoblastoma gene involved cancers, treating such kind of cancers and regulating the oncogenicity of other genes.

10 Claims, 9 Drawing Sheets

FIGURE 2

PPRB[110]- NUCLEAR PHOSPHOPROTEIN-THE RETINOBLASTOMA SUSCEPTIBILITY GENE PRODUCT

This application is a continuation of application Ser. No. 08/225,099, filed Apr. 8, 1994 issued as U.S. Pat. No. 5,578,701, Nov. 26, 1996; which is a continuation of application Ser. No. 08/079,207 filed Jun. 17, 1993 now abandoned; which is a continuation of application Ser. No. 07/914,039 filed Jul. 14, 1992 now abandoned; which is continuation of application Ser. No. 07/550,877 filed Jul. 11, 1990 now abandoned; which is a divisional of application Ser. No. 07/098,612 filed Sep. 17, 1987 (U.S. Pat. No. 4,942,123 Jul. 17, 1990).

This invention was made with Government support under grant No.: EY 05758 with the National Institute of Health and the University of California. The Government has certain rights in this invention.

FIELD OF THE INVENTION

This invention relates in general to a phosphoprotein product of the retinoblastoma susceptibility gene. In particular, this invention relates to a phosphoprotein ppRB[110] primarily located in the cell nucleus which has a DNA binding activity. The invention also relates to the amino acid sequence of the phosphoprotein and to the specific purified anti-retinoblastoma phosphoprotein antibody. The invention further relates to a method of diagnosing retinoblastoma and other retinoblastoma gene involved cancers, treating such kind of cancers and regulating the oncogenicity of other genes.

BACKGROUND

Retinoblastoma is a malignant tumor of the sensory layer of the retina. The neoplastic tumor is composed of primitive retinal cells, occurring often bilaterally, usually before the third year of life. It exhibits a familiar tendency. Retinoblastomas are characterized by small round cells with deeply staining nuclei, and elongated cells forming rosettes. They usually cause death by local invasion, especially along the optic nerves.

The retinoblastoma may be hereditary but also acquired. It is the most common intraocular tumor and represents one of the prototypes of inheritable cancers. The hereditary form is characterized by early age of onset and multiple tumor foci. Acquired form occurs later in life with single-unilateral tumor (*Proc. Natl. Acad. Sci.*, 68:820–823 [1971]; *Hum. Genet.*, 52:1–54 [1979]; *Science*, 223:1028–1033 [1984]).

The molecular mechanism of the formation of this tumor is unknown. Absence or inactivation of the retinoblastoma (RB) gene is believed to be the primary cause of this cancer (*Science*, 213:1501–1503 [1981]; *Science*, 223:1028–1033 [1984]; *Proc. Natl. Acad. Sci.*, 68:820–823 [1971]; *Nature*, 305:779–784 [1980]).

Susceptibility to hereditary retinoblastoma is transmissible to offsprings as an autosomal dominant trait with 90% penetrance, and the tumor is, therefore, a prototypic model for the study of genetic determination in cancer (*Am. J. Hum. Genet.*, 30:406–410 [1978]; *Cancer*, 35:1022–1026 [1975]).

There are at least two hypotheses related to the oncogenesis of retinoblastoma. The first hypothesis suggests that the tumor is caused by two mutational events (*Proc. Natl. Acad. Sci.*, 68:820–823 [1971]; *Cancer*, 35:1022–1026 [1975]). The other hypothesis proposes that autosomal dominant hereditary tumors, such as retinoblastoma, represent the inheritance of a defective regulatory or suppressor gene which normally regulates a group of transforming genes, most probably proto-oncogenes. Such genes, when active, would release the cell from its normal constraints on growth and therefore, if and when somatic mutation inactivates the normal suppressor gene, such as for example the RB gene, tumors can develop (*Proc. Natl. Acad. Sci.*, 70:3324–3328 [1973]).

Based on these hypotheses, hereditary retinoblastoma might arise from a precursor retinoblast cell, carrying one inherited defective allele which suffers an additional somatic mutation, while nonhereditary cases would require two somatic mutations in the same cell. Recent circumstantial evidence supports the existence of such cancer suppressor genes in retinoblastoma (*Nature*, 305:779–781 [1983]; *Proc. Natl. Acad. Sci.*, 83:7391–7394 [1986]; *Science*, 235:1394–1399 [1987]) as well as nephroblastoma also known as Wilm's tumor (*Nature*, 309:172–174 [1984]; *Nature*, 309:176–178 [1984]; neuroblastoma (*Cancer Res.*, 41:4678–4682 [1981]), osteosarcoma (*Proc. Natl. Acad. Sci.*, 82:6216–6220). retinoblastoma (*Hum. Genet.*, 52:1–54 [1979]; *Ann. Hum. Genet.*, 27:171–174 [1963]; *Am. J. Dis. Child*, 132:161–163 [1978]; *Science*, 208:1042–1044 [1980]; *Science*, 213:1501–1503 [1981]). Linkage was established to the gene for the polymorphic marker enzyme esterase D, which also maps to 13q14 (*Science*, 219:971–973 [1983]).

Additional evidence supporting this genetic assignment came from the pedigree of a family showing balanced chromosomal translocations in unaffected carrier parents and in some unaffected siblings but with an unbalanced chromosome 13 deletion in affected individuals (*Science*, 213:1501–1503 [1981]). This observations also indicated that the retinoblastoma susceptibility locus is able to function in the "trans" configuration.

The RB locus was further implicated in non-hereditary retinoblastoma by observing frequent abnormalities of chromosome 13 in tumor karyotypes and reduced esterase D activity in tumors (*Cancer Genet. Cytogenet.*, 10:311–333 [1983]; *Cancer Genet. Cytogenet.*, 6:213–221 [1982]). It has been proposed that inactivation of both alleles of the RB gene located in region 13q14 resulted in retinoblastoma. Such proposal was based in part on a case of hereditary retinoblastoma in which both RB alleles were inferred to be absent (*Science*, 219:973–975 [1983]). However, the assumption upon which this proposal was based, namely that the absence of esterase D activity in this case implied loss of both esterase D and RB genes, has been disproved (*Hum. Genet.*, 76:33–40 [1987]). Nonetheless, the other findings show that chromosome 13 markers which were heterozygous in somatic cells often became homozygous or hemizygous in retinoblastoma tumors, and that there are homozygous deletions in the 13q14 region in 3/37 retinoblastoma cell lines (*Nature*, 305:779–784 [1983]; *Proc. Natl. Acad. Sci.*, 83:7391–7394 [1986]). These experiments provide evidence that the proposed RB gene indeed functions in a recessive manner at the cellular level (*Science*, 235:305–311 [1987]; *Cancer Res.*, 46:1573–1580 [1986]) in distinction to the "dominant" activity of classical oncogenes (*Science*, 228:669–676 [1985]; *Nature*, 315:190–195 [1985]) as measured, for example, by transfection assays.

Thus, while an extensive research is devoted to inherited and acquired retinoblastoma and to its causes, the reliable method for diagnosing the embryo, fetus, or newborn baby for the predisposition to inherited retinoblastoma, or the child or adult for their susceptibility to development of acquired retinoblastoma, or the secondary tumors often accompanying retinoblastoma, is still not readily available. That is true mainly because the protein intermediating the function of the RB gene has not been known, isolated or identified.

Therefore, it would be advantageous to acquire more knowledge about the molecular and chemical properties of the retinoblastoma gene such as the gene sequence, identification of the gene's location, its cloning and the isolation. Isolation of the RB gene's protein product and the identification of its amino acid sequence would also be advantageous as well as preparation of specific anti-RB protein antibody, particularly because the RB gene function is intermediated by the specific RB protein which, in turn, can only be recognized in the tissue by the specific anti-RB protein antibody.

Both forms of retinoblastoma can now be treated and most patients can be followed through adult life. However, patients with hereditary retinoblastoma have an extraordinarily high risk for developing a second nonocular malignancies (*Ophthalmology*, 91:1351–1355 [1984]; *New Engl. J. Med.*, 285:307–311 [1971]; *Cancer*, 34:2077–2079 [1974]; up to 90% incidence within 30 years of initial diagnosis (*Ophthalmology*, 91:131–136 [1984]). The most frequently occuring secondary cancer is osteosarcoma, which is otherwise uncommon. In contrast, cured nonhereditary retinoblastoma patients show the same cancer rates as the general population. This finding is of considerable interest, since it implies that the RB gene may have a critical role in regulating other tumors as well.

Without complete isolation and identification of the RB gene and its protein product, an early diagnosis of the osteosarcoma or other RB secondary tumors, or the predisposition thereto, is unavailable.

Therefore, it would be advantageous to have available a means to diagnose the primary retinoblastoma or the susceptibility thereto, and to provide timely forewarning against the secondary molecular malignancies. The best way to achieve the above goals, is the by the identification of the amino acid sequence of the RB gene product protein, which protein, per se, is the intermediator of the RB gene regulatory function not only for retinoblastoma but also for its secondary tumorigenic regulating activity.

It is of obvious importance to understand the molecular nature of the RB gene, and the mechanism of its regulatory function through the protein product produced by retinoblastoma gene.

Recently, human retinoblastoma gene was successsfully cloned, identified and sequenced (*Science* 235:1394–1399 [1987]). The retinoblastoma gene was located in the chromosome 13 region 13q14:11 in the close proximity of the esterase D gene, also recently identified, cloned and sequenced (*Proc. Natl. Acad. Sci.*, 83:6790–6794 [1986]; *Proc. Natl. Acad. Sci.*, 83:6337–6341 [1986]). By chromosomal walking from esterase D gene, the retinoblastoma (RB) gene was identified on the basis of chromosomal location, homozygous deletion and tumor-specific alterations in expression. RB gene was shown to have 4723 nucleotides and encodes a messenger RNA (mRNA) of 4.8 kilobases (kb).

Transcription of RB DNA to RB mRNA was found to be abnormal in retinoblastoma patients. Transcription was either not detected at all, suggesting the absence or complete inactivation of the RB gene, or transcribed mRNA had shown decreased molecular size of about 4.0 kb, suggesting defective RB gene.

Sequence of RB complementary DNA (cDNA) clones yielded a single long open reading frame suggesting that it could encode a hypothetical protein of 816 amino acid. A computer-assisted search of a protein sequence data base revealed no closely related proteins suggesting a unique amino acid sequence of the predicted protein (*Science*, 235:1394–1399 [1987]). The predicted protein will seem to have several proline rich regions, similar to those previously observed in other nuclear oncogenes proteins such as proteins "myc" and "myb" (*RNA Tumor Viruses*, Cold Spring Harbor Laboratory, Cold Spring Harbor, N.Y. [1985]).

The hypothetical amino acid composition of the RB gene product protein seems to contain several distinguishable regions which were shown to be similar to the other oncogenic proteins. This finding suggests that the RB gene protein product could have similar regulatory functions as these other oncogene proteins.

However, without chemical and molecular characterization on the RB gene protein product and without specific anti-RB protein antibody, the further elucidation of the RB protein in regulation of tumorigenesis is impossible.

Therefore, it would be advantageous to identify the amino acid sequence of the RB gene, to determine its subcellular localization and to determine whether it has DNA binding activity.

It would also be advantageous to obtain the exact amino acid sequence of the RB gene product, to prepare or isolate the portion or the whole RB protein in purified form, and to obtain a specific anti-retinoblastoma protein antibody which would specifically recognize the retinoblastoma protein in the tissue. Such antibody would then be employed as a diagnositc tool to recognize the presence or the absence of the RB gene product protein. Thus, the anti-RB protein antibody would diagnose the normal or abnormal protein of the RB gene in several different kinds of human cancer.

It is, therefore, the object of this invention to provide a complete amino acid sequence of the RB gene protein product.

It is another object of this invention to biochemically characterize the RB gene protein product and to determine its molecular weight.

It is still another object of this invention to determine the subcellular localization of the RB gene protein product.

It is yet another object of this invention to provide a metabolically labeled radioactive RB gene protein product.

It is a further object of this invention to provide a specific anti-retinoblastoma protein polyclonal antibody.

It is still a further object of this invention to provide a diagnostic method for hereditary predisposition to retinoblastoma in fetus, embryo and newborn, or for the susceptibility in the later age to acquire a secondary cancer associated with the retinoblastoma. Retinoblastoma gene involved cancers such as osteosarcoma, fibrosarcoma, glioblastoma and breast cancer.

It is still a further object of this invention to provide a method for treatment of cancerogenous growth through the regulation of growth promoting genes and by genetic manipulation.

DETAILED DISCLOSURE OF THE INVENTION

All references cited in this application are hereby incorporated by reference and made part of this application.

Experimental evidence indicates that complete inactivation of the RB gene is required for tumor formation, and hence indicates a new mode of function for the RB gene as a suppressor of the cancer phenotype.

Since the gene action is generally intermediated by its protein product, it appears that the RB gene protein product would have a gene-regulatory activity.

Therefore, obtaining the complete amino acid sequence of the RB gene protein product, specific anti-retinoblastoma protein antibody, its biochemical characterization, subcellular localization and its DNA binding activity, would be of utmost importance for further elucidation of the RB gene regulatory and oncogenic activity.

The complete amino acid sequence of the retinoblastoma gene protein is the subject of previously noted article in Science, 235:1394–1399 [1987]. The specific polyclonal anti-retinoblastoma protein antibody was prepared. The RB protein was localized by subcellular fractionation and its evolutionary conservation was shown. DNA binding activity of the RB gene protein was proven.

Amino acid sequence of any protein is determined by the genetic code of the particular gene responsible for that particular protein. Therefore, in order to isolate the protein, to determine its exact amino acid sequence and to determine its physiological function in the body, it is necessary to isolate and localize the responsible gene, to clone it and to sequence the cDNA which are useful in identification of the gene's specific protein product.

Using the method of chromosomal walking from other chromosome 13 markers, retinoblastoma gene and encoding of the amino acid sequence was identified at 13 chromosome, 13 q14:11 region. By using esterase D cDNA clones and by screening the genomic and cDNA libraries, several clones were obtained. From these clones, two cDNA overlapping clones RB-1 and RB-2 of 1.6 kb and 0.9 kb, respectively, were identified in human cDNA libraries. Later on, another clone RB-5 was also identified.

In the process of developing this invention, first, the RB-1 clone was hybridized with 4.8 kb mRNA transcript in human fetal retina and placenta. In retinoblastoma samples, RB-1 clone either detected an abnormal mRNA transcript or the mRNA transcripts were not observed at all. Subsequently identified RB-5 clone, with a 3.5 kb insert, gave identical results as RB-1 in mRNA hybridization. Restriction enzyme analysis suggested that RB-5 and RB-1 clones overlapped in a 0.4 kb region and both together defined a DNA segment of about 4.6 kb, a size close to that of the normal RB mRNA transcript.

Nucleotide sequence analysis of clones RB-1 and RB-5 was performed by the dideoxy-terminator method described in Proc. Natl. Acad. Sci., 74:5463–5467 [1977] and yielded the reconstructed complete cDNA sequence. Different deletion templates were generated by the "cyclone" method (Ibid) in single stranded M13 phage clones, which yielded greater than 95% of the sequence. The remaining gaps were sequenced by primer extension in both strands. The complete sequence identified in this way contained 4,523 nucleotides.

An open reading frame was present from the 5' end to base 2688, with numerous additional in-frame stop codons further downstream. Translation from the first methionine codon (base 241) yielded a hypothetical protein of 816 amino acids (94,000 daltons in size). The second in-frame methionine was at base 346. Since the nucleotide sequence surrounding the first ATG is not typical of other known mRNA (Nucleic Acid Res., 12:857–863 [1984]), the start codon assignment should be regarded as tentative. A computer search of the National Biological Research Foundation protein sequence database detected no strong homology with any of more than 4000 published amino acid sequences. However, a number of nucleic acid-binding proteins and viral proteins showed weak sequence homology, with a yeast DNA-directed RNA polymerase (Cell, 42:599–610 [1985]) having the highest homology score.

The predicted protein sequence included ten potential glycosylation sites (CRC Crit. Rev. Biochem., 10:307–366 [1981]) but a candidate transmembrane domain (at least 20 consecutive hydrophobic residues) was not found. The amino acid hydropathy plot showed a mildly hydrophobic region near the putative amino terminus and a hydrophilic region at the carboxyl terminus. Two pairs of short amino acid sequences were identified that were bracketed by cysteine and histidine residues in the manner of metal-binding domains found in nucleic acid-binding proteins (Science, 232:485–487 [1986]). A region of 54 amino acids from position 663 to 716 contains 14 proline residues or about 26% such proline-rich regions have also been observed in nuclear oncogene proteins myc and myb (RNA Tumor Viruses, Cold Spring Harbor Laboratory, Cold Spring Harbor [1985]). While the significance of these observations is not well established, they suggest that the RB gene product may be a nucleic acid-binding protein.

Taking into consideration the previous findings, and the fact that the nucleotide sequence analysis of RB cDNA clones demonstrated a long-open reading frame encoding a hypothetical protein with features suggestive of a DNA binding function, it was an initial object of this invention to identify and characterize the RB protein to be used as an antigen for obtaining specific antibody and to determine its predicted DNA binding.

RB protein antigen was prepared by expressing the fusion protein in E. coli. For that purpose, a 20 kb polypeptide fragment of the RB gene was fused with TRYP E protein and the fusion protein has been expressed in E. coli.

From the hypothetical RB protein sequence data with 816 amino acids and molecular weight of approximately 98 kD, three pATH plasmids that express TRYP E fusion protein were constructed. The complete cDNA clone was divided into three portions, namely into fragments 0.7 kb, 0.9 kb and 1.8 kb. These three fragments contained the coding sequence of RB cDNA. Plasmid pATH3-0.9RB was constructed from the fragment 5' 0.9 kb inserted into EcoRI—EcoRI site of pATH3. Plasmid pATH3-0.7RB was constructed by inserting middle 0.7 kb fragment of RB-1 clone into EcoRI—EcoRI site of pATH3, and the plasmid pATH3-1.8 RB was constructed by inserting 3' 1.8 kb fragment into BglII—BglII site of pATH3 vector. Orientation was confirmed by detail mapping of the restriction enzyme sites.

The recombinant plasmids pATH3-0.9RB, pATH3-0.7RB and pATH3-1.8RB were then transformed into E. coli mm 294 and grown in M9 minimal medium which was supplemented with tryptophan preferably of concentration of about 20 mg/ml. The culture mixture was diluted from 1:10 to 1:150, preferably 1:100, with M9 medium, with casamino acids and ampicillin added. The procedure for recombinant plasmid construction is described in J. Virol, 49:132–141 [1984]. The fusion of the fragments into pATH vector frames at the site of restriction enzymes is described in Proc. Natl. Acad. Sci., 83:4685–4689 [1986].

Only one of the three pATH3 constructs, namely pATH3-0.7RB expressed the fusion protein. The obtained fusion protein had a molecular weight of 57 kD. Since the molecular weight of TRYP E is known to be 37 kD, 20 kD protein portion of the fusion protein was derived from the RB.

The other two plasmid constructs produced no protein at all, not even TRYP E itself. Since RB clones contain many hypothetical protease cleavage sites, the inability to produce protein in E. coli was not surprising and was probably due to instability of the fusion protein.

Using the above described procedure for fusing pATH3 with RB fragment, large quantities of the fusion protein were prepared and purified by preparative SDS polyacrylamide gel electrophoresis according to procedure described in *Nature,* 227:680–685 [1970]. The fusion protein was eluted by overnight extraction and SDS and soluble acrylamide were removed by dialysis. The proteins were then concentrated.

Purified fusion protein was used as an antigen in generating specific anti-RB protein antibody.

The specific rabbit polyclonal antibody against RB protein were prepared by the procedure described generally in *Proc. Natl. Acad. Sci.,* 83:6790–6794 [1986].

Rabbits were repeatedly injected, preferably at 14 day intervals with 1–20 μg, preferable 10 μg, of purified fusion protein mixed with complete Freund's adjuvant (initial injection) and then given booster injections of the same amount of the fusion protein in incomplete Freund's adjuvant (repeated injections). Complete Freund's adjuvant generally consists of an emulsion of the antigen, in this case the fusion protein, in saline and a mixture of an emulisifying agent, such as for example Arlacel A, in mineral oil with killed mycobacteria. Incomplete Freund's adjuvant is the same except that it does not have the mycobacteria.

The injections were repeated until sufficiently high titer of anti-fusion protein was detected, approximately for two months, to react with both TRYP E and the fusion protein. To enrich for antibodies recognizing only RB determinants, two or more affinity columns were prepared using a methods generally described in *Proc. Natl. Acad. Sci.,* 37:575–578 [1951], and in *Immunoadsorbents in Protein Purification, Scand. J. Immunol., Suppl.* 3 [1976]. At least one column was loaded with TRYP E protein and at least one column was loaded with the fusion protein. Both colums were appropriately precycled. Antibody was passed first through the fusion protein-Sepharose column and eluted with glycine buffer of pH 2.3. The eluate was neutralized and passed through the TRYP E column several times to remove antibody specifically directed against TRYP E. The purified anti-RB IgG antibody was used for immunoprecipitation or immunostaining, for localization of RB protein and will be equally useful for diagnostic identification of RB protein in human tissue samples.

To identify the RB protein, several human cell lines known to have either normal or altered RB gene expression were selected.

LAN-1 neuroblastoma cell line normal human fibroblasts, human hepatoma Alexander cell line and osterosarcoma U20S cell line were used as positive controls containing normal RB mRNA. All these cells were obtained from the American Type Culture Collection (ATCC), Inc. depository. Cell lines with expected shortened or absent RB mRNA, such as retinoblastomas cell lines Y79 (ATCC), RB355 (Gifted from Robert Philips, Toronto, Canada), WERI-1, WERI-24, and WERI-27 (Gifted from T. Sery Wills' eye hospital, Phliladelphia) were used as negative controls.

All normal human cell lines as described above and all cells from five retinoblastomas were labeled with $^{35}$S-methionine and immunoprecipitated with preimmune rabbit antibody IgG or rabbit anti-RB IgG.

Cells from all human cell lines were metabolically labeled with $^{35}$S-methionine according to procedure described in *J. Virol,* 38:1064–1076 [1981]. Labeled cell mixtures were immunoprecipitated with 1-20 ul, preferably 10 ul, of from 50 ug/mi–200 ug/ml, preferably 100 ug/ml of anti-RB antibody IgG using the procedure described in *J. Virol,* 38:1064–1076 [1981].

In all control cell lines a protein doublet with apparent molecular weight of 110–114 kD was detected. In retinoblastoma cell lines, or in cells immunoprecipitated with preimmune serum the protein doublet was not detected.

The RB proteins immunoprecipitated with rabbit anti-RB IgG were analyzed by SDS/polyacrylamide gel electrophoresis and into auto-radiographed. The results are shown in FIG. 1. The RB protein presence is visible at approximately 110 kD region in lanes 2–5 which illustrate the immunoprecipitation of the normal positive, i.e. RB protein containing cell lines labeled with $^{35}$S-methionine. Lane 1 is the control line of neuroblastoma cell immunnoprecipitated with the preimmune, hence without anti-RB protein antibody, rabbit IgG. Lanes 6–10 are obtained by immunoprecipitation of labeled $^{35}$S-methionine cell lines from five retinoblastomas. There is no RB protein present in any of these cell lines.

The absence of antigenically detectable RB protein in retinoblastoma cells supports the notion that oncogenicity by mutant RB genes is achieved through complete loss of gene product function even in those cell lines containing shortened RB mRNAs.

The hypothetical protein predicted from the nucleotide sequence was expected to have MW about 98 kD. The immunoprecipitated protein has a MW about 110–114 kD. Complete RB protein amino acid sequence is illustrated in FIG. 2. This complete sequence is obtained from the newly reconstructed clone which contains the most 5' end stretch missing in the original cDNA clone (*Science,* 1987). The first and second initiation methionines are boxed and alanine and proline clusters are underlined.

The amino acid sequence (FIG. 2) is written in the abbreviation code recognized in the art. Single-letter abbreviations for the amino acid residues are: A=Alanine, C=Cysteine, D=Aspartic acid, E=Glutamic acid, F=Phenylalanine, G=Glycine, H=Histidine, I=Isoleucine, K=Lysine, L=Leucine, M=Methionine, N=Asparagine, P=Proline, Q=Glutanine, R=Arginine, S=Serine, T=Threonine, V=Valine, W=Tryptophane and Y=Tyrosine.

RB cDNA sequence (*Science,* 235:1394–1399 [1987]) contained a long open reading frame from nucleotide 1 through 2688, which when translated from the first methionine codon yielded a hypothetical protein of 816 amino acids and molecular weight 98 kD. Recently another isolated RB cDNA clone contained an additional 234 base pairs on the 5' end. The revised RB cDNA sequence (FIG. 2) still maintained the same open reading frame as in the original clones, and an additional methionine codon was found at nucleotide 139. When this methionine was used as an initiation codon, the predicted RB protein had 928 amino acids and a molecular weight of 110 kD—identical to the apparent M.W. determined by SDS-PAGE. The additional 5' sequence contains a GC-rich region that translation into an unusual cluster of alanine and proline residues (FIG. 2).

Discrepancies between actual and apparent molecular weights on SDS-PAGE may be explained by secondary protein modifications. Several potential N-linked glycosylation sites are present in the predicted amino acid sequence seen in FIG. 2. However, when LAN-1 cells were grown in medium supplemented with $^{14}$C-galatose or $^3$H-glucosamine, labeled RB protein was not detected despite prolonged autoradiography. In addition, digestion of $^{35}$S-labeled RB protein by Endoglycosidase H according to method described in *J. Biol. Chem.,* 250:8569–8579 [1975], did not result in a reduction of apparent molecular weight.

When the neuroblastoma cells LAN-1 were metabolically labeled with $^{32}$P-phosphoric acid and immunoprecipitated, the immunoprecipated protein ran as a single band with molecular weight indentical to the $^{35}$S-labeled RB protein. The results, illustrated in FIG. 3, show Lanes 2+3 showing a $^{35}$S-labeled band at 110–114 kD and Lane 5-$^{32}$p-labeled band at 110–114 kD. Lanes 1 ($^{35}$S) and 4 (32p) are immunoprecipitated with preimmune rabbit IgG. When the aliquots of RB samples labeled with $^{35}$S-methionine were digested overnight with Endoglycosidase H, there was no detectable reduction of molecular weight 110–114 kD. The above findings prove that the retinoblastoma is a phosphoprotein of MW 110–114 kD. The phosphoprotein was therefore named ppRB$^{110}$.

The RB gene was detected in other vertebrates at the DNA level (*Science*, 235:1394–1399 [1987]) suggesting that the RB gene is present in many species during the evolution and further suggesting an important physiological role.

The cells from several vertebrate species, such as QT6 (quail), NIH/3T3 (mouse), Rat-2 (Rat) and cos (monkey) were labeled with $^{32}$P-phosphoric acid as described previously and proteins were immunoprecipitated with anti-RB IgG using the same procedure as used for human cells. As shown in FIG. 4, antigenically related proteins were detected in all cells with apparent similar molecular weights of 108 kD in quail, 120 kD in mouse, 128 kD in rat and 108–110 kD in monkey, as compared to 110–114 kD in human cells.

Antigenically related proteins with varied molecular weights observed in different vertebrate species such as quails, mice, rats and monkeys suggest that the RB protein is conserved through the evaluation, most probably in proportion to evolutionary relatedness. Since both antigens and molecular weights are simultaneously conserved in these vertebrate species, it is likely that the RB gene product is present and functionally similar in other species as well.

The predicted whole amino acid sequence of the ppRB$^{110}$ protein has several characteristics similar to those appearing in other oncogenes. Therefore, the subcellular localization of the ppRB$^{110}$ was investigated by cellular fractionization.

Two methods were essentially employed to find out the distribution of ppRB$^{110}$ between the nuclear, cytoplasmic, or cell membrane fractions.

In agreement with the chemical characterization the ppRB$^{110}$ sequence suggesting possible DNA binding, it was determined that 85% of ppRB$^{110}$ was found in the nuclear fraction, with proportionally small amount (less than 10%) of the ppRB$^{110}$ was located in membrane. There was no detectable presence in the cytoplasmic fraction.

To further substantiate that the ppRB$^{110}$ is localized primarily in the nucleus, the osteosarcoma cell lines U20S known to have an advantageous cell morphology for immunohistochemical staining were used. As an experimental group, the U20S cells were immunoprecipitated with anti-ppRB$^{110}$ IgG. As a control group, the U20S cells were immunoprecipitated with preimmune IgG. Both groups were then incubated with rhodamine conjugated goat anti-rabbit IgG obtained commercially from Sigma. Immunofluorescence was observed in cells reacted with anti-ppRB$^{110}$ IgG, namely in the cell nucleus (FIG. 5, Bi). Cells reacted with preimmune control did not show any fluoresenece (FIG. 5, Bii).

The subcellular localization of ppRB$^{110}$ in the nuclear fraction suggests that the RB protein plays an important regulatory function in regulating other genes and has a DNA-binding activity.

Certain cell lines, particularly those from tumors others than retinoblastoma, such as neuroblastoma LAN-1 cells were radioactively labeled with $^{32}$P-phosphoric acid. Cellular lysates of these labeled cell mixtures were separated by single or double stranded calf thymus DNA-cellulose columns according to the method described in *Mol. Cell. Biol.*, 6:4450–4457 [1986].

The results obtained suggest that the ppRB$^{110}$ binds only to a limited number of DNA sites that are easily saturated. It has been previously shown that other proto-oncogenes such as c-myc, n-myc, c-myb and c-fos are nuclear phosphoproteins with DNA binding activity (*Mol. Cell. Biol.*, 6:4450–4457 [1986]), *Nature*, 296:262–266 [1982]). Oncogenic activation of these proto-oncogenes occurs by deregulation of gene expression or by structural modification, and the gene product is essential for oncogenicity.

The ppRB$^{110}$ absence, and not the presence, appears to be oncogenic due to the partial or complete inactivation of the RB gene. Therefore, the presence of the ppRB$^{110}$ somehow suppresses the oncogenic activity of other genes and disallows the malignant cell growth. The ppRB$^{110}$ is thus an important regulatory protein which may prevent and inhibit, by its presence, and trigger, by its absence, the malignant growth. Thus, the ppRB$^{110}$'s importance is in regulating other genes. The absence or loss of ppRB$^{110}$ mediate oncogenicity.

The utility of the current invention is several fold.

First, the presence or absence of the ppRB$^{110}$ shall serve as a diagnostic tool in determination of presence or predisposition to the retinoblastoma and other RB gene involved tumors of the human and animal fetus, embryo or newborn babies. Such early diagnosis will allow an early warning and treatment of retinoblastoma and other tumors with the possibility of preventing development of the secondary tumorigenesis.

In practice, the use of this invention to diagnose the presence or predisposition to retinoblastoma, will be through immunoscreening of the tissue biopsy with specific anti-ppRB$^{110}$ antibody. The bioptic tissue will be radioactively labeled with $^{35}$S-methionine, $^{32}$P-phosphoric acid or any other convenient radioisotope and immunoscreened, as described above or the proteins extracted form bioptic tissue were blotted on nitrocellulose filter and probed with labeled antibody according to method known in the art as Western blotting.

It is expected, that such readily available diagnostic method will be used particularly for screening families with the history of hereditary retinoblastoma. The diagnostic method, however, is also intended to be used for prophylactic prenatal and postnatal screening. Moreover, the diagnostic method will be useful also for prediction of the development of secondary cancer, such as for example osteosarcoma, fibrosarcoma, glioblastoma, breast cancer, etc., whether or not connected with retinoblastoma.

The other intended use is for tumorigenesis suppression where the absent ppRB$^{110}$ will be provided through the molecular induction and gene transplanting of the RB cDNA to the individual in need of ppRB$^{110}$.

Still another use of the current invention is the suppression of the cancerogenous growth providing intact the RB gene directly to the tumor cells, which cells in turn will produce ppRB$^{110}$ which will affect the other tumorous cells.

BRIEF DESCRIPTION OF FIGURES

FIG. 2 is the complete RB cDNA nucleotide sequence and predicted amino acid sequence of the RB protein.

DETAILED DESCRIPTION OF FIGURES

Figure 1:
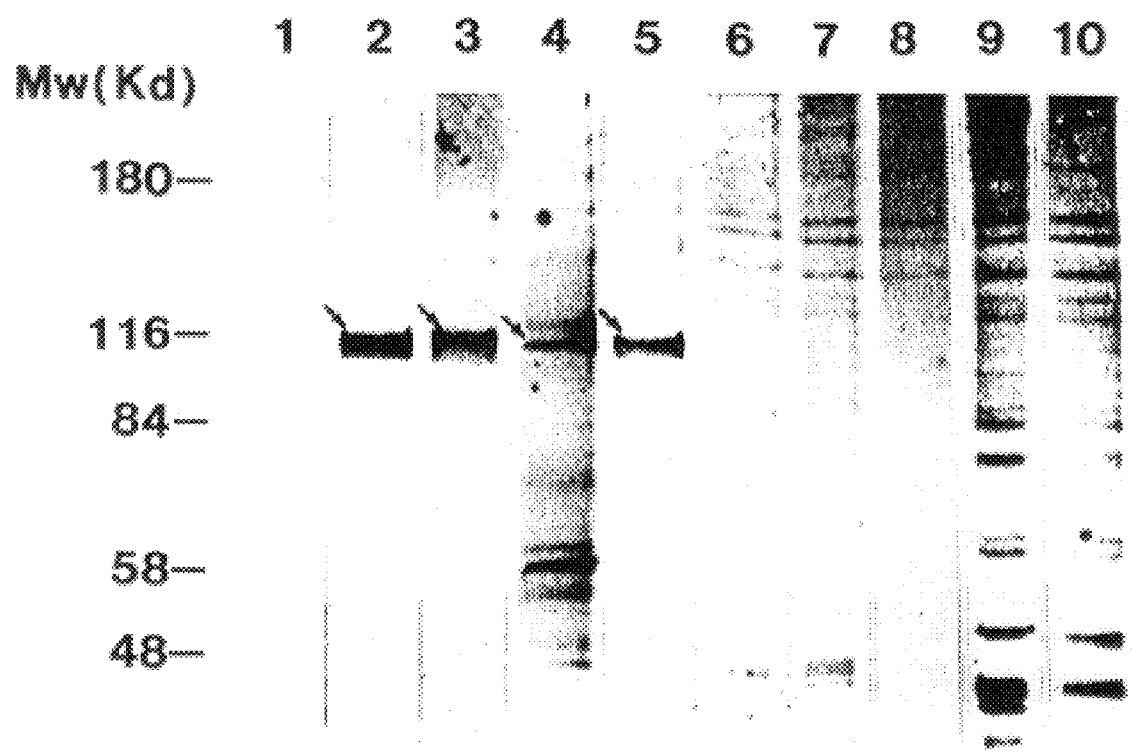
FIG. 1 is the chromatogram showing RB proteins in various cell lines.

FIG. 1 is the chromatogram illustrating the identification of RB proteins by immunoprecipitation with rabbit anti-RB IgG in various cell lines. Human cells such as neuroblastoma LAN-1 (Lanes 1 and 2), Alexander hepatoma (Lane 3), osteosarcoma U20S (Lane 4), normal fibroblasts (Lane 5), and five retinoblastomas (Lanes 6 to 10) were labeled with $^{35}$S-methionine and immunoprecipitated with preimmune rabbit IgG (Lane 1) or rabbit anti-RB IgG (Lanes 2-10). The immunoprecipitates were analyzed by 7.5% SDS-polyacrylamide gel electrophoresis and autoradiographed.

Figure 2:
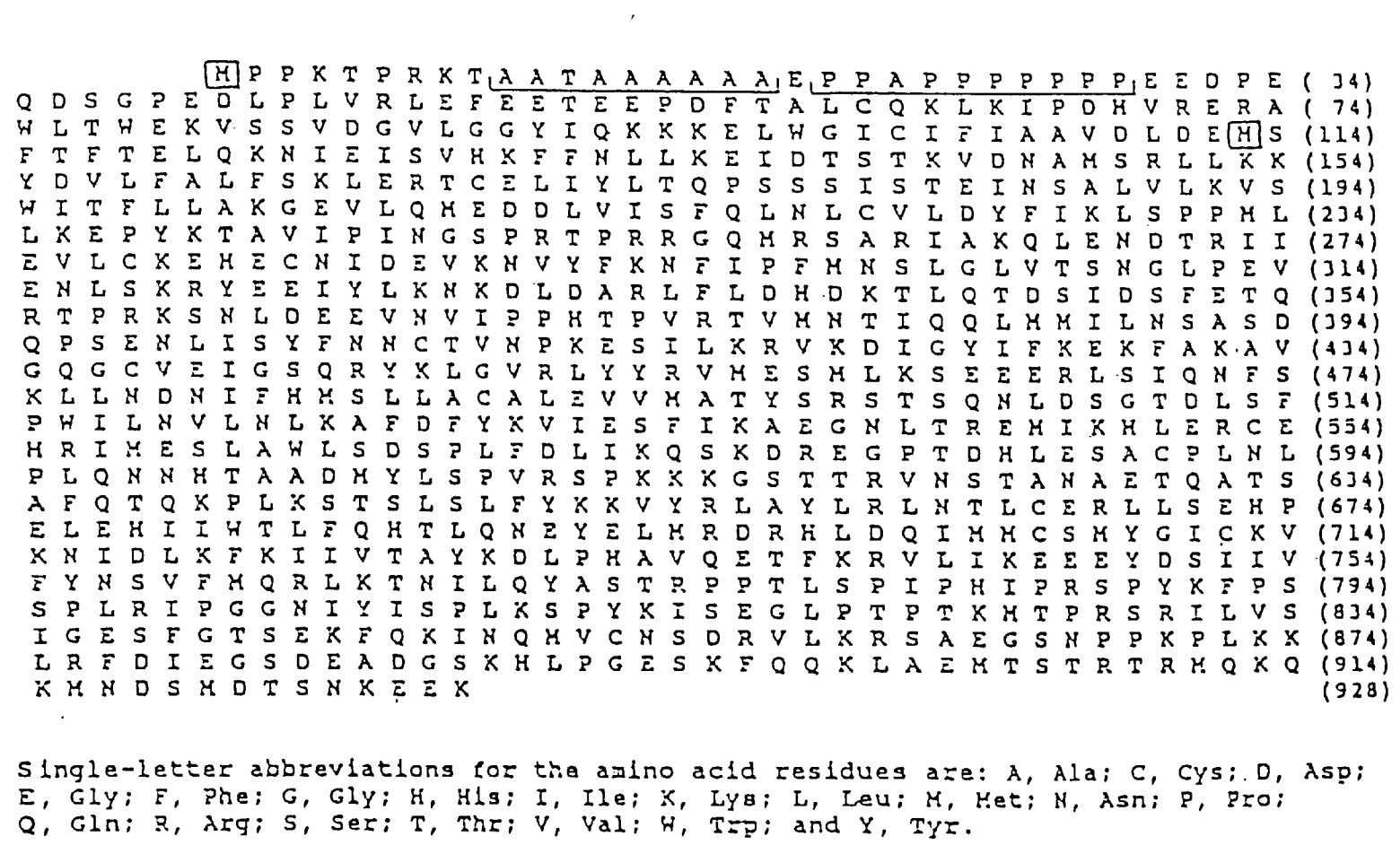

FIG. 2 is the complete RB cDNA nucleotide sequences and predicted amino acid sequences of the RB protein. The most 5' ~240 nucleotides were obtained from a cDNA clone from retinoblastoma cell line Y79. Nucleotide sequences from this clone and the original normal RB clones were aligned by sequence overlap. The first and second initiation sites are boxed, and alanine and proline clusters underlined.

Figure 3:
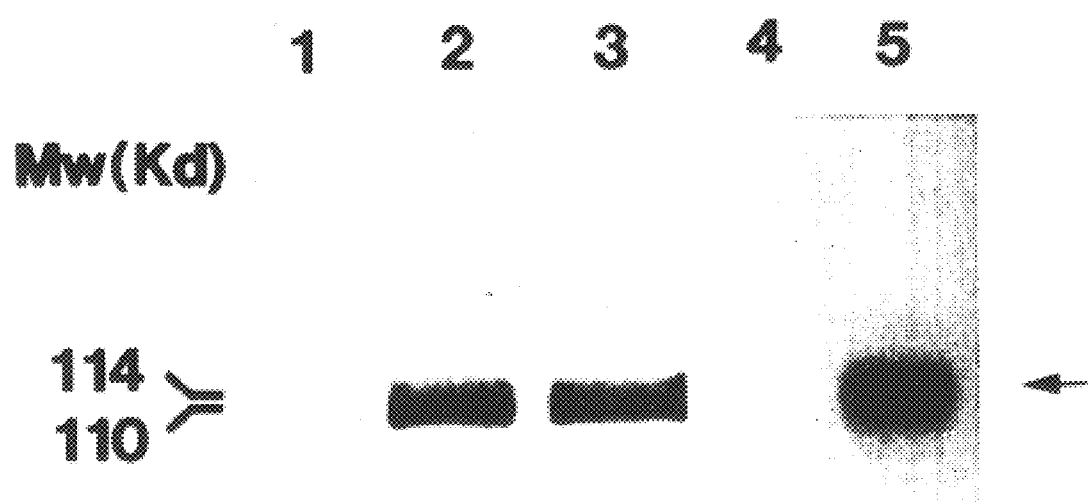
FIG. 3 is the chromatogram illustrating the immunoprecipitation of the RB gene product.

FIG. 3 is the chromatogram illustrating the modifications of the RB protein. LAN-1 cells were labeled with $^{35}$S-methionine (lanes 1–3) or $^{32}$P-phosphoric acid (0.5 mci/ml) (lanes 4 and 5) for three hours. Cellular lysates were immunoprecipitated with preimmune rabbit IgG (lane 1 and 4) or anti-RB IgG (lanes 2, 3 and 5). Aliquots of $^{35}$S-methionine-labeled RB proteins were digested with Endoglycosidase H (ICN ImmunoBiologicals) overnight (lane 3). These immunoprecipitates were then analyzed by 7.5% SDS-polyacrylamide gel as described in FIG. 1. The RB gene product was found to be phosphorylated but not glycosylated.

Figure 4:
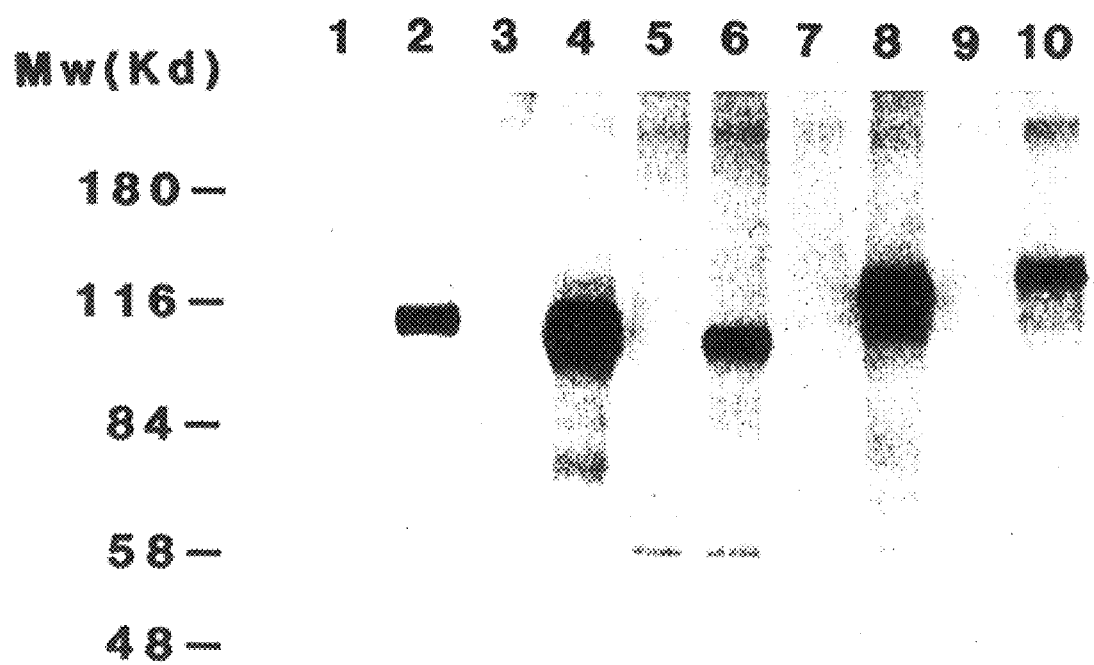
FIG. 4 is the chromatogram showing a conservation of the RB gene product in different vertebrates.

FIG. 4 is the chromatogram illustrating a conservation of the RB gene product in different vertebrate species. Cell lines of human neuroblastoma, LAN-5, (Lanes 1 and 2), monkey, cos, (lanes 3 and 4), quail fibroblast, QT6, (Lanes 5 and 6), mouse fibroblast, NIH/3T3, (Lanes 7 and 8), and rat fibroblast, rat-2, (Lanes 9 and 10) were labeled with $^{32}$P-phosphoric acid and immunoprecipitated with preimmune IgG (odd numbered lanes) or anti-RB IgG (even numbered lanes) and analyzed as described in FIG. 1. RB proteins of similar but distinguishable sizes were found among different vertebrate pieces.

Figure 5A:
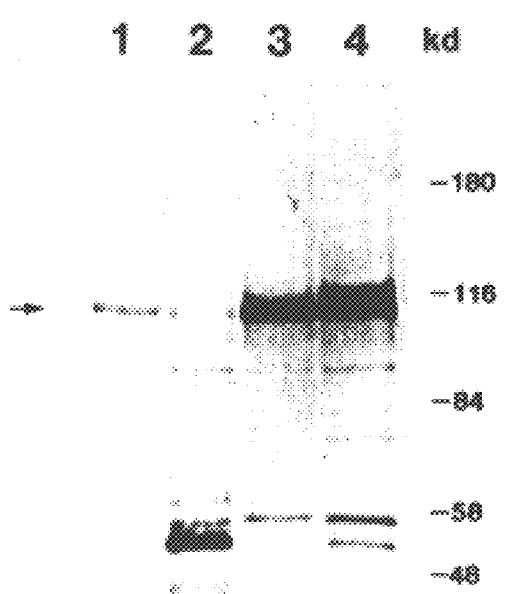
FIG. 5A is the chromatogram showing the subcellular localization of the RB protein.

FIG. 5A is the chromatogram showing a localization of the RB protein. $^{35}$S-methionine labeled LAN-1 cells (Lane 4) were fractionated into membrane (Lane 1), cytoplasm (Lane 2) and nucleus (Lane 3) and protein was immunoprecipitated with anti-RB IgG. The immunoprecipitates were then analyzed by SDS-PAGE as described for FIG. 1.

Figure 5B:
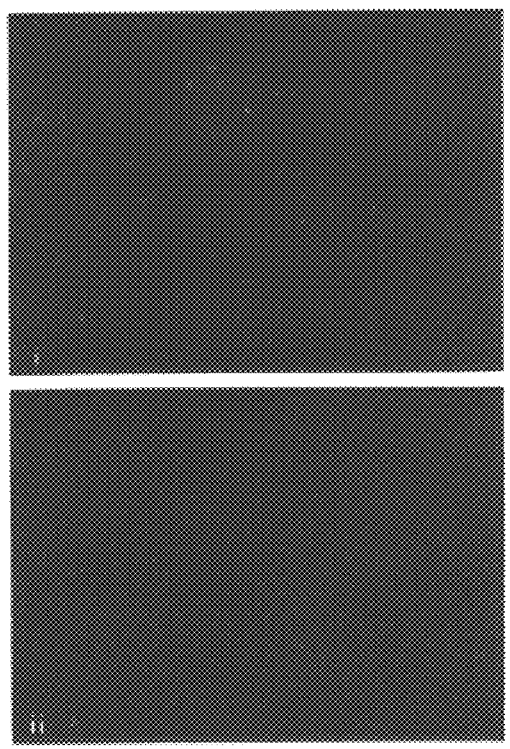
FIG. 5B is the immunofluorescence chromatogram showing the RB protein localization within osteosarcoma cell line U20S.

FIG. 5B is the chromatogram showing the results of the immunofluorescence studies of RB protein localization within osteosarcoma cell line U20S. Cells reacted with (i) anti-RB IgG and (ii) preimmune rabbit IgG. Most fluorescence was found within the nucleus.

Figures 6A, 6B:
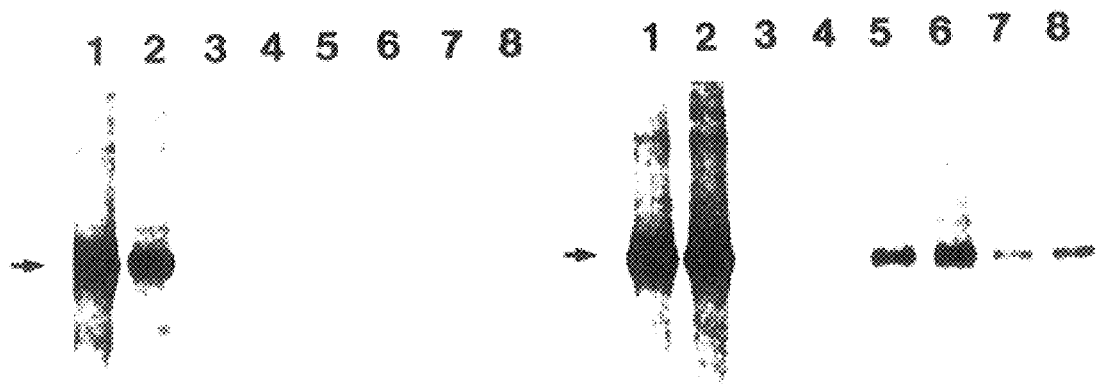
FIG. 6A is the picture of the column chromatography of the RB gene protein on single stranded DNA cellulose.
FIG. 6B is the picture of the column chromatography of the RB gene protein on double stranded DNA cellulose.

FIG. 6A is the picture of the column chromatography of the RB gene phosphoprotein in single stranded DNA cellulose. Protein lysates of the human neuroblastoma cells LAN-1 were metabolically labeled with $^{32}$P-phosphoric acid and passed through a single stranded DNA columns and eluted with increasing gradient of NaCl (Lane 3=0.05; Lane 4=0.1; Line 5=0.2; Lane 6=0.3; Lane 7=0.5 and Lane 8=1.0 M NaCl). Lane 1 shows the whole cell lysate immunoprecipitated with anti-RB IgG.

FIG. 6B is the picture of the column chromatography of the RB gene phosphoprotein in double stranded DNA cellulose. Protein lysates of the human neuroblastoma cells LAN-1 were metabolically labeled with $^{32}$P-phosphoric acid and passed through a double stranded DNA columns and eluted with increasing gradient of NaCl (Line 3=0.05; Line 4=0.1; Line 5=0.2; Line 6=0.3; Line 7=0.5 and Line 8=1.0 M NaCl). Line 1 shows the whole cell lysate immunoprecipitated with anti-RB IgG.

Figure 7A:
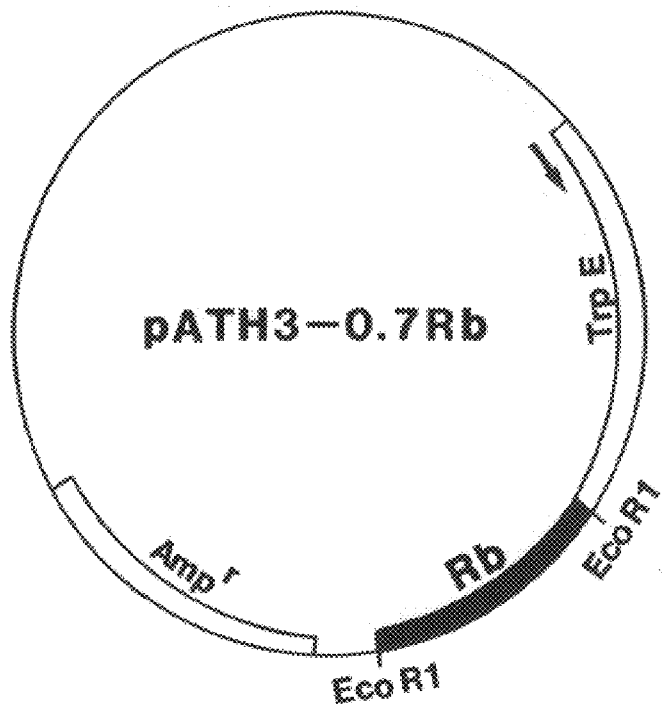
FIG. 7A is the drawing showing a production of TRYP E-RB fusion protein.

FIG. 7A is the drawing illustrating the production of the TRYP E-RB fusion protein. EcoRI—EcoRI cDNA RB fragment (0.7 kb) was fused in-frame into the EcoRI site of pATH3 vector. Orientation was confirmed by detailed restriction enzyme mapping. The recombinant plasmid was then transformed into E. coli mm294.

Figure 7B:
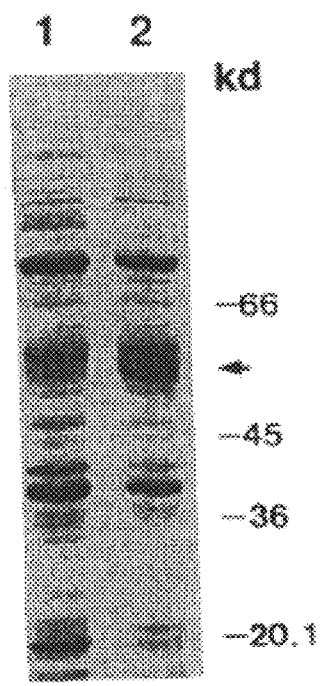
FIG. 7B is the picture of the polyacrylamide gel electrophoresis of the TYRP E-RB fusion protein.

FIG. 7B is the picture of the polyacrylamide gel electrophoresis of the recombinant TRYP E-RB fusion protein. The recombinant plasmid was then transformed into E. coli mm294, and grown in M9 minimal medium supplemented with 20 mg/ml of tryptophan. The culture was diluted to 1:100 in M9 plus casamino acids and ampicillin. At an optical density at 600 nm of 0.2, a 1:1000 dilution of a 10 mg/ml stock of indoleacrylic acid in 100% ethanol was added to induce the expression of the TRYP E promoter. Bacteria cells were pelleted and boiled in Laemnli gel sample buffer for 15 minutes and analyzed by polyacrylamide gel electrophoresis. Gel was then stained with Coomassie blue. A 58 kD protein was found in induction culture (Lane 2) but not in control culture (Lane 1).

Figure 8A:
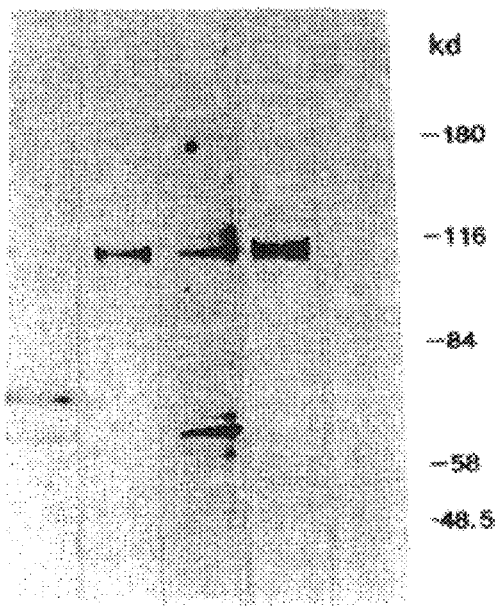
FIG. 8A is the chromatogram showing a immunoprecipitation of RB protein with anti-RB IgG of the several human cell lines.

FIG. 8A is the chromatogram showing immunoprecipitation of RB protein/anti-RB protein IgG from the various human cell lines. $^{35}$S-methionine-labeled cells extracts prepared from a human hepatoma Alexander cell line (Lane 1), human osteosarcoma cell line, U20S (Lane 2), normal human fibroblast (Lane 3), human neuroblastoma cell line, LAN-5 (Lane 4), and from neuroblastoma lysates precipitated by preimmune rabbit IgG (Lane 5) were immunoprecipitated with purified rabbit anti-RB IgG. Doublet bands with apparent molecular weight about 110-114 kD were observed in Lanes 1–4.

Figure 8B:
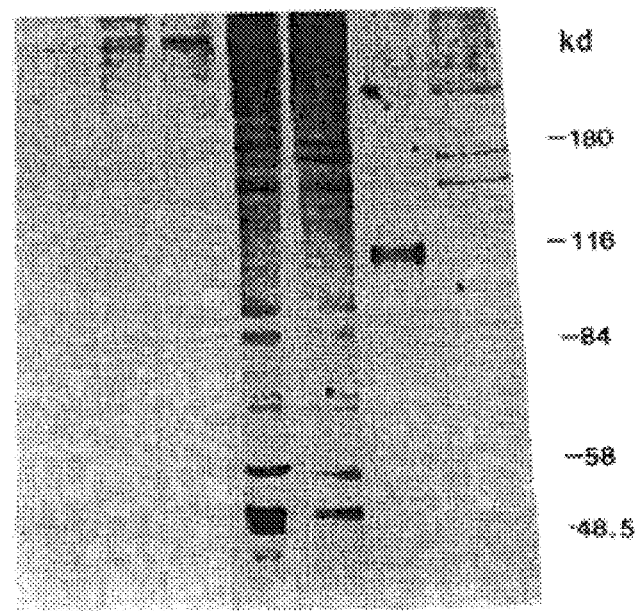
FIG. 8B is the chromatogram showing immunoprecipitation of RB protein with anti-RB IgG in retinoblastoma cell lines.

FIG. 8B is the chromatogram showing immunoprecipitation of RB protein/anti-RB protein IgG from the several retinoblastoma cells.

Cell extracts from five different retinoblastoma cell lines were labeled with $^{32}$S-methionine and immunoprecipitated with purified rabbit anti-RB IgG. Doublet bands present in cell lines from hepatoma, osteosarcoma, fibroblastoma and neuroblastoma were absent in all five retinoblastoma cell lines RB 355 (Lane 1), Y79 (Lane 2), WERI-1 (Lane 3), WERI-24 (Lane 4), and WERI-27 (Lane 5), human neuroblastoma cell line LAN-5 (Lane 6) and from neuroblastoma lysates precipitated by preimmune rabbit IgG (Lane 7). The RB protein was identified based on these results.

Figure 9:
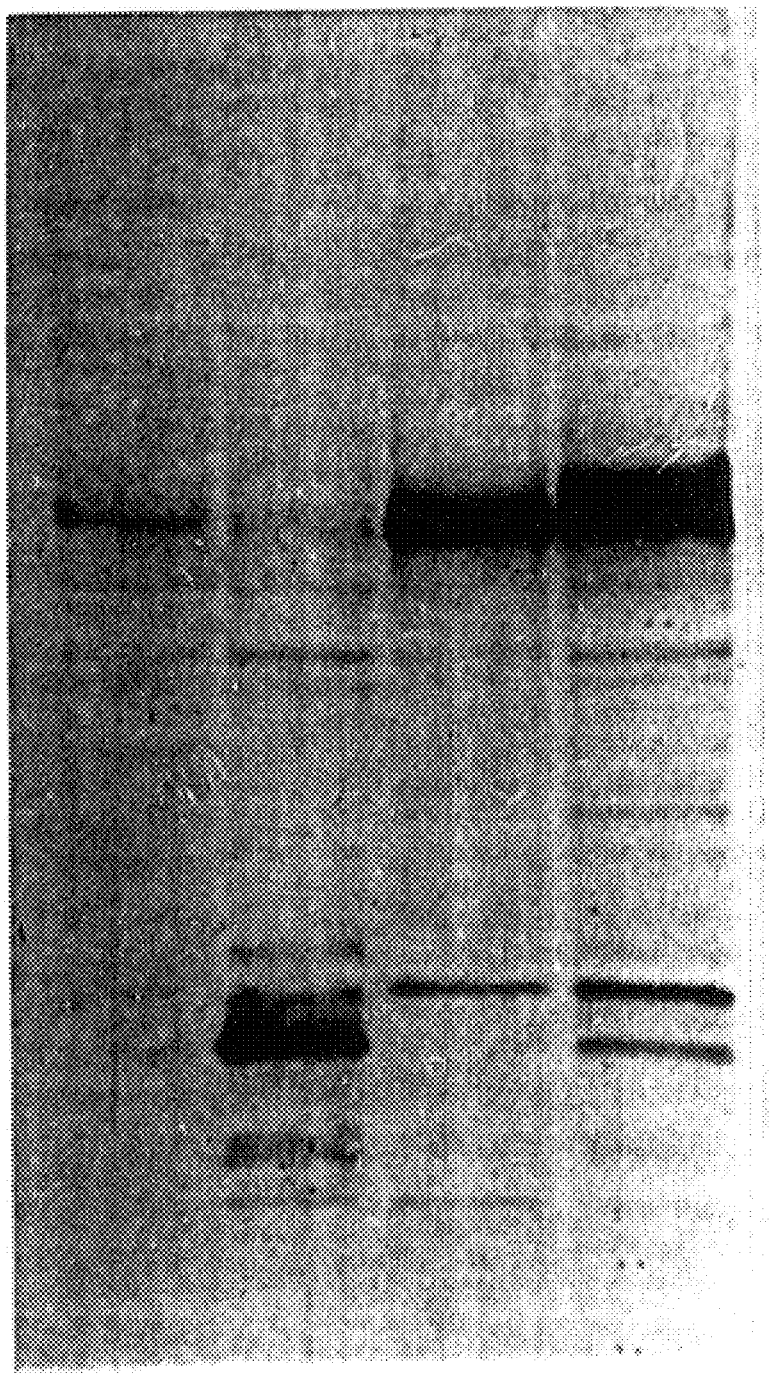
FIG. 9 is the chromatogram illustrating the biochemical fractionation of the RB protein.

FIG. 9 is the chromatogram showing a biochemical fractionation to demonstrate the localization of the RB protein. $^{35}$S-methionine labeled whole cells of LAN 5 (Lane 4) was fractionated into membrane (Lane 1), cytoplasm (Lane 2) and nucleus (Lane 3) and were subsequently immunoprecipitated with rabbit anti-RB IgG. The majority of the $RB^{110-114}$ protein was found in the nucleus with minor portions in membrane or cytoplasm.

The following examples further illustrate and present a preferred embodiments of the invention disclosed herein. The examples are not intended to limit the scope of the invention.

EXAMPLE 1

Preparation of Recombinant Fusion Protein

Recombinant fusion protein has been prepared for use as an antigen for immunization.

The conserved 5' 0.9 kb, middle 0.7 kb and 3' 1.8 kb regions of RB cDNA were subcloned into an inductible, high-level TRYP E expression vectors, pATH-3 (University of California, San Diego) using a standard procedure described in *Moleculor cloning: A Laboratory Manual*, Cold Spring Harbor Laboratory, Cold Spring Harbor, N.Y.

Three RB cDNA subfragments containing the coding sequence, namely 5' 0.9 kb (EcoRI—EcoRI), middle 0.7 kb (EcoRI—EcoRI of RB-1) and 3' 1.8 kb (BglII—BglII) were fused in frame with pATH3 vectors, respectively. The TRYP E-RB gene product of pATH3-0.7 plasmid was expressed in *E. coli* using a method described in *J. Virol*, 49:132–141 [1984]. pATH3-0.7 RB was constructed as illustrated in drawing 7A. cDNA RB fragment was inserted in-frame into the EcoRI endonuclease site of pATH-3 plasmid. Orientation was confirmed by detail restriction enzyme mapping. The recombinant plasmid was transformed into *E.coli* mm294 and grown in M9 minimal medium supplemented with 20 mg/ml of tryptophan. The culture was diluted to 1:100 in M9 plus casamino acids and ampicillin. At an optical density at 600 nm of 0.2, a 1:1000 dilution of a 10 mg/ml stock of indoleacrylic acid in 100% ethanol was added to induce the expression of the TRYP E promoter.

Bacteria cells were pelleted and boiled in Laemmli gel sample buffer for 15 minutes and analyzed by polyacrylamide gel electrophoresis. Gel was then stained with Coomassie blue. Large quantities of fusion protein were prepared and purified through preparative polyacrylamide gel electrophoresis and eluted by overnight extraction. SDS and soluble acrylamide were removed by dialysis. The proteins were then concentrated and mixed with adjuvant for immunization of rabbits. About 6 mg protein was recovered which was subsequently used for immunization of rabbits.

The expression in *E. coli* produced, after induction, a 57 kD fusion protein comprising 20% of total *E. coli* protein. pATH-0.7 expressed a fusion protein with MW of 57 kD, of which 3.7 kD was TRYP E and 20 kD was RB-derived. The other two plasmids produced no protein at all.

Production of the TRYP E-RB fusion protein can be seen in FIG. 7A and the results of the PAGE/gel electrophoresis in 7B. A 58 kD protein was found in induction culture (Lane 2) but not control culture (Lane 2).

EXAMPLE 2

Anti ppRB$^{110}$—Specific Antibody

Two rabbits were immunized with the TRYP E ppRB$^{110}$ fusion protein obtained in Example 1 following a standard protocol.

New Zealand Red rabbits were initially injected with 10 µg of purified TRYP E ppRB$^{110}$ fusion protein mixed with complete Freund's adjuvant and then given booster injections of 10 µg of TRYP E ppRB$^{110}$ fusion protein in incomplete Freund's adjuvant. The booster injections were repeated for several months until high titers of antibody were detected by immunoprecipitation analysis according to *Proc. Natl. Acad. Sci.*, 76:4350–4354 [1979].

Two months later, both rabbits produced high titers of antibodies that reacted with both TRYP E and the fusion protein. The rabbits were bled and the blood was collected into plastic containers and clotted. The serum was obtained by centrifugation at 1000 g for 10 minutes. Rabbit anti-ppRB$^{110}$ immunoglobulin (IgG) was purified by passing the antisera through the two affinity columns. To enrich for antibodies recognizing only RB determinants, two affinity columns were prepared, one with TRYP E protein and the other with the fusion protein. The antiser was passed through the fusion protein-Sepharose column and eluted with 0.1M glycine HCl buffer (pH 2.3). The eluate was passed through the TRYP E column several times to remove antibody directed against TRYP E using the same buffer. The elution was repeated several times. Antibody prepared through the above steps was serially diluted and the dilution sufficient for immunoprecipitation of RB protein in $1.5 \times 10^6$ cells were determined. This purified anti-RB antibody was used in all subsequent experiments for immunoprecipitation or immunostaining and to immunoprecipitate RB protein in several cell lines which were previously demonstrated to contain intact RB mRNA according to procedure of Example 3.

EXAMPLE 3

Immunoprecipitation Idenification of RB Protein with Anti-RB Antibody

A standard protocol was followed as described in *J. Virol.*, 38:1064–1076 [1981].

LAN-1 neuroblastoma cell lines normal human fibroblasts, human hepatoma Alexander cell line and osterosarcoma U20S cell line which are containing normal RB mRNA were used as positive controls. All these cells were obtained from the American Type Culture Collection, Inc. depository. Cell lines with expected shortened or absent RB mRNA, such as retinoblastomas cell lines Y79, RB355, WERI-1, WERI-24, and WERI-27 were used as negative controls. These cell lines were obtained as described above.

To label cellular proteins with 35S methionine, about $1.5 \times 10^6$ cells in 60-mm petri dishes were starved by incubation at 37° C. for 30 minutes in methionine-free medium and then incubated in 3 ml of methionine-free medium supplemented with $^{35}$S-methionine (150 uCi/ml) for three hours. All subsequent operations were at 4° C. Cell extracts were prepared in lysis buffer containing 25 mM Trishydrochloride (pH 7.4), 50 mM NaCl, 0.2% Nonidet P-40, 0.5% deoxycholate and 200 units/ml of Aprotinin inactivator. 0.02% SDS was also added at the beginning of lysis. The lysates were clarified by centrifugation at 4° C. at 20,000×g for 15 minutes.

Immunoprecipitation was carried out with 5 ul of preimmune rabbit antisera, followed by absorption to formalin-fixed *Staphylococus aureus* obtained from The Enzyme Center, Inc. To supernatant of each experimental sample was added 10 ul of 100 ug/ml of anti-ppRB[110] IgG and to supernatant of each control sample was added 10 ul of the preimmune sera for control. Protein A sepharose beads (Sigma) were then added. Immunoprecipitates were subsequently washed with 1) lysis buffer, 2) 1 M NaCl in lysis buffer, 3) 0.15 M NaCl in lysis buffer, and 4) lysis buffer to remove nonspecifically bound proteins. The immunoprecipitated proteins were analyzed by 7.5% SDS-polyacrylamide gel electrophoresis and autoradiographed. Gels of $^{35}$S-labeled proteins were fluorographed at –70° C. after impregnation with acetic acid-based 2.5-diphenyloxazole.

The results are illustrated in FIG. 1. The protein with MW 110–114 kD was found to be immunoprecipitated with anti-ppRB[110] IgG.

EXAMPLE 4

Characterization of the RB Gene Product

To further characterize the ppRB[110] protein, the cells were labeled with $^{32}$P-phosphoric acid or with $^{14}$C or $^{3}$H-glucosamine and subsequently digested with Endoglycosidase H.

To test for protein phosphorylation, LAN-1 cells were metabolically labeled with $^{32}$P-phosphoric acid. To label LAN-1 cells with 32p, around 1.5×10$^6$ cells in 60-mm petri dishes were starved by incubation at 37° C. for 80 minutes in phosphate-free medium and then incubated for 1 to 2 hours in 2 ml of phosphate-free medium supplemented with 32PO$_4$$^3$-(1m ci/ml) medium. Cell extracts were prepared in lysis' buffer containing 25 mM Tris-hydrochloride of ph 7.4, 50 mM NaCl, 0, 2% Nonideb P-40, 0.5% deoxycholate and 200 units/ml of kallikrein inactivator obtained from Calbiochem. The lysate was clarified at 4° C. at 20,000×g for 20 min.

Immunoprecipitation was carried out with anti-ppRB[110] IgG according to standard procedure. Immunoprecipitate was absorbed to formalin-fixed *Staphylococcus aureus* obtained from the Enzyme Center and subsequently washed with 1) lysis buffer; 2) 1M NaCl, 10 mM Tris-hydrochloride (pH 7.4) and 0.1% Nonidet P-40; 3) 0.15 mM NaCl, 10 mM Tris-hydrochloride (pH 7.4), 0.1 Nonidet P-40; and 4) lysis buffer.

The immunoprecipitated proteins were prepared for electrophoresis following the procedure described in *J. Virol,* 36:617–621 [1980].

Immunoprecipitated protein ran as a single band with molecular weight identical to that of $^{35}$S-labeled ppRB[110] protein indicating that the RB protein is a phosphoprotein.

EXAMPLE 5

Subcellular Localization Of The ppRB[110] Human neuroblastoma cells LAN-1 were labeled with $^{32}$S-methionine as described in Example 3, and fractionated into membrane, cytoplasm and nucleus. The labeled protein was subsequently immunoprecipitated with anti-RB IgG. cell fractionation protocol is essentially adapted from that described in *J. Cell. Biol.,* 97:1601–1611 [1983].

Two to five 100-mm plates containing a total of 2.0×10$^7$ to 7.5×10$^7$ LAN-1 cells were metabolically labeled with $^{35}$S-methionine for 2–3 hours prior to use. All subsequent procedures were performed at 4° C. Cells were rinsed twice with phosphate-buffered saline (PBS), scraped into PBS, and pelleted for 5 minutes at 375×g in a table top centrifuge. Half the cells were resuspended in lysis buffer for the whole cell lysate. The remaining cells were rinsed once in hypotonic RSB buffer (10 mM HEPES pH 6.2, 10 mM NaCl, 1.5 mM MgCl$_2$, 200 units/ml Aprotinin) and then resuspended in RSB. The cell suspension was homogenized by 20 strokes in a tight fitting Dounce homogenizer, and volume was adjusted to exactly 3 ml with RSB buffer. The homogenate was centrifuged at 1,500 rpm in a Sorvall HB4 rotor at 375×g for 10 minutes, and the pellet was resuspended in lysis buffer to generate the nuclear fraction. The supernatant was centrifuged in thick-walled polyallomer tubes in a Beckman SW50.1 rotor at 35,000 rpm (150,000×g) for 90 minutes. The pellet was resuspended in lysis buffer to generate the membrane fraction, while the supernatant was adjusted to 1× lysis buffer concentration to produce the cytoplasmic fraction. All four fractions were then assayed for RB protein content as illustrated in Example 3.

The immunoprecipitates were analyzed by 7.5% SDS-polyacrylamide gel electrophoresis and autoadiographed.

The results are summarized and illustrated in FIG. 5A.

In alternative, the following fractionation method was used. All procedures were performed at 0 to 4° C. Two to five 100-mm plates containing a total of 2.0×10$^7$ to 7.5×10$^7$ LAN-1 cells were rinsed twice with phosphate-buffered saline (PBS), scraped into PBS, and pelleted for 1 min. at 1,000×g in a clinical centrifuge. After the pellet was rinsed once with hypotonic TKM buffer (20 mm Tris pH7.1, 5mM KCl, 1 mM MgCl$_2$, 1% Aprotinin), the cells were dispersed and swollen in TKM for 15 min. The cell suspension was homogenized by 20 strokes in a tight fitting Dounce homogenizer. The volume was adjusted to exactly 3 ml with TKM buffer, and samples were removed for analysis by immunoprecipitation.

Nuclear pellet was generated by low-speed centrifugation, and the supernatant from this initial centrifugation was subjected to high-speed centrifugation to obtain a precipitate and a soluble fraction. To obtain a nuclear pellet, the homogenate was centrifuged at 1,500 rpm in a Sorvall HB4 rotor (375×g) for 10 min. at 0° C., and the crude nuclear pellet was suspended in 1 ml of TKM.

This pellet was then homogenized five times in the Dounce homogenizer and aspirated three times through a 1 ml syringe fitted with a 25-gauge needle. The suspension was then pelleted as described above, suspended in TKM buffer and aspirated again five times through the same syringe.

After a final centrifugation, the nuclear pellet was suspended in TM buffer and analyzed for RB protein content and for subcellular markers. The original postnuclear supernatant (PNS) and the supernatants from the nuclear pellet washes were pooled and centrifuged in thick-walled polyallomer tubes in a Beckman SW50.1 rotor at 38,000 rpm (150,000×g) for 90 minutes at 0° C. to generate particulate (P$_{150}$) and soluble (S$_{150}$) fractions. The fractions were then adjusted to equal volumes with TKM buffer and assayed directly for RB protein and subcellular markers.

Plasma membrane content was determined by measuring 5' nucleotidase. The samples were taken up in TKM buffer and incubated in an assay mixture containing 10 mM MgCl$_2$, 0.1 mM AMP, 100 mM glycine (pH 9.0), and 2 uCi of $^3$H-adenosine in the supernatant determined by liquid scintillation counting (Ibid). The soluble protein in each fraction was determined assaying for lactate dehydrogenase activity according to *Proc. Natl. Acad. Sci.,* 48:2123–2130 [1962], and the endoplasmic reticulum content was measured with an assay for NADH diaphorase according to procedure described in *Biochem. Biophys. Acta.,* 233:334–347 [1971].

The results are illustrated in FIG. 9. Using methods of biochemical fractionation and immunofluorescence (Example 6), the RB protein was determined to be localized primarily in the nucleus.

A majority (about 85%) of $^{35}$S-labeled protein was located in the nuclear fraction while a minor portion (less than 10%) was associated with membrane. There was no detectable RB protein within the cytoplasmic fraction, or secreted into the medium.

EXAMPLE 6

Subcellular Localization of ppRB$^{110}$ Measured By Immunofluorescence

Human osteosarcoma cell line U20S, obtained from American Type Culture Collection, Inc., were used for immunofluorescent staining.

About $10^4$ U20S cells were seeded onto 12-mm glass cover slips and used 18 hours later for immunofluorescent staining. The cells were washed once with PBS buffer and fixed with cold acetone for 10 minutes at room temperature. Fixed and permeabilized cells were hydrated in PBS for 1 to 2 minutes. Each cover slip was incubated with 200 ul of rabbit anti-RB IgG (1:20 dilution) or preimmune serum in a moist chamber for 45 minutes at room temperature. After three washes in PBS, the cover slips were incubated with 200 ul of rhodamine-conjugated goat anti-rabbit IgG (25 ug/ml) obtained from Sigma for 45 minutes at room temperature. The cover slips were again washed extensively in PBS and viewed with a Zeiss photomicroscope III.

Alternatively, immunofluorescent staining of LAN-1 neuroblastoma cell lines was carried out as follows. $10^4$ LAN-1 cells were seeded onto 12-mm glass cover slips and used 18 hours later for immunofluorescent staining. The cells were washed once with PHEM buffer consisting of 0.06 M Pipes, 0.025 M HEPES, 0.01 M EGTA, 0.002 M MgCl$_2$, pH 6.9 and fixed with 2% paraformaldehyde in PHEM buffer for 20 minutes at room temperature. Fixed and permeabilized cells were washed once in PHEM buffer and three times in PBS. Each cover slip was incubated with 12 ul of a 1:80 dilution of a rabbit anti-RB IgG, or preimmune serum in a moist chamber for 45 minutes at room temperature. After three washes in PBS, the cover slips were incubated with 12 ul (25 ug/ml) of fluorescein isothiocyanate conjugated goat and anti-rabbit immunoglobulin G obtained from Sigma Chemical Co., for 45 minutes at room temperature. The cover slips were again washed extensively in PBS and incubated at room temperature for 45 minutes with rhodamine-conjugated phalloidin (20 ug/ml). The stained preparation was mounted in PBS-glycerol (1:9) containing the antibleaching agent p-phenylenediamine and viewed with a Zeiss photomicroscope III.

The results are illustrated in FIG. 5B and are similar to those obtained by biochemical fractionation described in Example 5. The fluorescence was present mainly within the nucleus and the preimmune control was negative.

EXAMPLE 7

DNA Binding Activity Assay

Two DNA binding assays, DNA-Sepharose column chromatography and filter binding, were used.

These two methods have been previously used in studies of myc (*Nature*, 296:262–266 [1982]), N-myc (*Embo J.*, 4:2627–2633 [1985]), and myb proteins (*Cell*, 40:983–990 [1985]).

Sepharose Column Chromatography

To test DNA binding activity of the RB protein, double-stranded and single-stranded calf thymus DNA coupled onto Sepharose 2B obtained from Pharmacia was employed.

Protein lysates of the human neuroblastoma LAN-1 cells were metabolically labeled with $^{32}$P-phosphoric acid and separated on single-stranded (A) and double-stranded (B) DNA cellulose columns namely with 0.05, 0.1, 0.2, 0.3, 0.5 and 1.0 M NaCl. Column chromatography separation of the RB gene protein product on single stranded and double stranded DNA cellulose is illustrated in FIG. 6. LAN-1 cells labeled with $^{32}$P-phosphoric acid for three hours were lysed in lysis buffer and clarified as described previously. The supernatant was diluted 10-fold with loading buffer (1 mM DTT, 0.5% NP40, 10 mM potassium phosphate, 10% glycerol pH 6.2, Aprotinin 200 units/ml). The diluted extract was then applied to calf-thymus DNA-cellulose columns (Pharmacia) *Mole. Cell Biol.*, 6:4450–4457 [1986], equilibrated with loading buffer containing 50 mM NaCl. After allowing binding to occur for 40 minutes, the column was washed with 5ml of loading buffer and then eluted with buffer containing 1 mM DTT, 10 mM Tris-HCl, pH 8.0 with increasing NaCl concentration from 0.05 to 1.0 M. The eluates were then immunoprecipitated with rabbit anti-RB IgG. The whole cell lysates and flow-through immunoprecipitated with anti-RB IgG, respectively, served as the controls. Fractions were then analyzed by immunoprecipitation as described in Example 3.

The results are illustrated in FIG. 6.

EXAMPLE 8

Diagnostic Determination of the ppRB$^{110}$ in the Tissue

Tumor cells disassociated from biopsy tissue from the subject was labeled with $_3$5S methionine or $^{32}$P-phosphoric acid an immunoprecipitated with anti-ppRB$^{110}$ IgG according to the procedure of Example 3. Alternatively, protein lysates extracted from bioptic tissue can be directly diagnosed using the Western blotting analysis probed with either radioactive labeled or non-radioactive labeled anti-RB specific antibody. The presence or absence of immunoprecipitated proteins serves as a diagnostic tool in determination of retinoblastoma or other diseases controlled by the retinoblastoma gene.

What is claimed is:

1. An isolated and purified protein with a molecular weight of 110 to 114 kilodaltons wherein said polypeptide is a product of a retinoblastoma gene.

2. The protein of claim 1, wherein the protein is a phosphoprotein.

3. The protein of claim 1 which has an amino acid sequence consisting of:

```
MPPKTPRKTAATAAAAAAEPPAPPPPPPPEEDPE

QDSGPEDLPLVRLEPEETEEPDFTALCQKLKIPDHVRERA

WLTWEXVSSVDGVLGGYIQKKKELWGICIFIAAVDLDEMS

PTFTELQKNIEISVHKFFNLLKEIDTSTKVDNAMSRLLKK

YDVLFALPSKLERTCELIYLTQPSSSISTEINSALVLKVS

WITFLLAKGEVLQMEDDLVISFQLHLCVLDYFIKLSPPHL

LKEPYKTAVIPIHG8PRTPRRGQMRSARIAKQLENDTRII
```

-continued

```
EVLCKEHECNIDEVKNVYFKNFIPFMNSLGLVTSNGLPEV

ENLSKRYEEIYLKNKDLDARLFLDHDKTLQTDSIDSFETQ

RTPRKSNLDEEVNVIPPHTPVRTVMVTIQQLMMILHSASD

QPSEHLISYFNNCTVNPKESILKRVKDIGYIFKEKPAKAV

CQGCVEIGSQRYKLGVRLYYRVMESMLKSEEERLSIQNFS

KLLNDNIPHMSLLACALEVVMATYSRSTSQNLDSGTDLSF

PWILNVLNLKAFDFYKVIESFIKAEGNLTREMIKHLERCZ

HRIMESLAWLSDSPLFDLIXQSKDREGPTDHLESACPLHL

PLQNNHTAADMYLSPVRSPKKKGSTTRVNSTANAETQATS

AFQTQKPLKSTSLSLPYKKVYRLAYLRLNTLCERLLSEHP

ELEHIIWTLPQHTLQNEYELMRDRHLDQIHMCSHYGICKV

KNIDLKPKIIVTAYKDLPHAVQETFKRVLIKEEEYDSIIV

PYNSVFMQRLKTNILQYASTRPPTLSPIPHIPRSPYKPPS

SPLRIPGGHIYISPLKSPYKISEGLPTPTKMTPRSRILVS

IGESFGTSEKFQKINQMVCNSDRVLKRSAEGSNPPKPLKK

LRFDIEGSDEADGSKHLPGESKPQQKLAEMTSTRTRMQKQ

KMHDSMDTSNKEEK.
```

4. A fission protein comprising a polypeptide with a molecular weight of 1110 to 114 kilodaltons which is a product of a retinoblastoma gene.

5. The phosphoprotein of claim 2 which is isolated primarily from a cell nucleus.

6. An isolated protein which is the product of a retinoblastoma gene isolated by a process comprising the following steps:
 (a) reacting a composition containing a protein which is a product of the retinoblastoma gene with an anti-retinoblastoma protein antibody;
 (b) isolating an antibody-retinoblastoma protein complex from the composition; and,
 (c) isolating the retinoblastoma protein from the antibody.

7. The isolated protein of claim 6, wherein the antibody is a polyclonal antibody.

8. An isolated protein which is the product of a retinoblastoma gene isolated by a process comprising the following steps:
 (a) reacting a composition containing a protein which is a product of the retinoblastoma gene with a DNA;
 (d) isolating the DNA-retinoblastoma protein complex from the composition; and,
 (e) isolating the retinoblastoma protein from the DNA.

9. The isolated protein of claim 8, wherein the DNA is coupled to a solid surface.

10. The isolated protein of claim 9, wherein the solid surface is selected from the group consisting of Sepharose and a filter.

\* \* \* \* \*